United States Patent [19]
Yoshizumi et al.

[11] Patent Number: 4,737,362
[45] Date of Patent: Apr. 12, 1988

[54] HAIR TREATMENT COMPOSITION

[75] Inventors: Hajime Yoshizumi, Takatsuki; Teruo Amachi, Takarazuka; Takaaki Kusumi, Suita; Takaharu Tanaka, Osaka; Hiroshi Ishigooka, Ibaraki, all of Japan

[73] Assignee: Suntory Limited, Osaka, Japan

[21] Appl. No.: 648,287

[22] Filed: Sep. 7, 1984

[30] Foreign Application Priority Data

Sep. 22, 1983 [JP] Japan ................................ 58-174085

[51] Int. Cl.$^4$ .............................................. A61K 37/54
[52] U.S. Cl. ............................ 424/94.6; 424/DIG. 4; 514/852
[58] Field of Search ............................... 424/94, 70, 93

[56] References Cited
U.S. PATENT DOCUMENTS 3,939,260  2/1976  Lafon ...................................... 424/28

FOREIGN PATENT DOCUMENTS 0097810  1/1984  European Pat. Off. .
1242794  6/1967  Fed. Rep. of Germany .
2074498  9/1971  France .

OTHER PUBLICATIONS

Patent Abstracts of Japan, vol. 6, No. 73 (C-101) [951], 8th May, 1982; & JP-A-57 11 905 (Eiji Suga) 21-01-1982.

Primary Examiner—J. R. Brown
Assistant Examiner—John W. Rollins, Jr.
Attorney, Agent, or Firm—Burns, Doane, Swecker & Mathis

[57]  ABSTRACT

A hair treatment composition containing, as an effective ingredient, lipase. This hair treatment composition can effectively prevent the generation of dandruff and itching and can also effectively accelerate the growth of hair.

6 Claims, No Drawings

HAIR TREATMENT COMPOSITION

BACKGROUND OF THE INVENTION

1. Field of the Invention

The present invention relates to a novel hair treatment composition suitable for use in preventing the generation of dandruff (or scurf) in hair and itching in the scalp and in accelerating the growth of hair. More specifically, it relates to a novel hair treatment composition containing, as an effective ingredient, lipase.

2. Description of the Prior Art

The possession of a healthy and profuse head of hair throughout life is the ambition of most human beings. Various kinds of hair dressings, including hair treatment compositions, have been used for slowing down or stopping epilation or depilation (i.e., the involuntary loss of hair and subsequent balding). It is considered that epilation is related with abnormalities in the capillary vessels, hair follicles, and epidermis skin due to changes in, for example, the endocrine system, autonomic nervous system, and blood circulation system. To prevent or alleviate the above-mentioned abnormalities, various agents, for example, skin hyperergasia agents such as female hormones, vitamins, amino acids, crude drug extracts, various bactericides, keratolysis agents, and sensitizing dyes, and peripheral nervous stimulators such as menthol have been used in hair tonic compositions. However, at present there are no truly effective agents for alleviating epilation, accelerating the growth of hair, and further alleviating or curing the generation of dandruff and itching of the scalp.

SUMMARY OF THE INVENTION

Accordingly, an object of the present invention is to provide a novel hair treatment composition capable of effectively supressing the generation of dandruff and itching of the scalp and also accelerating the growth of hair.

In accordance with the present invention, there is provided a hair treatment composition containing, as an effective ingredient, lipase.

DESCRIPTION OF THE PREFERRED EMBODIMENTS

The inventors previously made a detailed comparative study of the microflora of the scalps of persons with healthy hair and those of persons with unhealthy hair (e.g., persons with dandruff, itching of the scalp, and abnormal depilation) and found *Staphylococcus capitis* constituted all or most of the microflora in the scalp of those with healthy hair. Contrary to this, in the scalp of those with unhealthy hair, they found no substantial amount of *Staphylococcus capitis* in the microflora, but found microorganisms such as *Staphylococcus epidermidis* and *Pityrosporum ovale*. The inventors further clarified that the cells of *Staphylococcus capitis* have a lipase activity and testosterone 5α-reductase (i.e., "5α-reductase") inhibitory activity. The term "5α-reductase" denotes an enzyme which reduces testosterone to 5α-dihydrotestosterone.

Based on these findings, the inventors suggested that the above-mentioned activities are closely correlated with the growth effect of hair (see U.S. patent application Ser. No. 505,273 or European Patent Application No. 83303654.4).

The inventors further studied the correlation of the above-mentioned lipase activity and 5α-reductase inhibitory activity with hair growth and found that products containing fatty acids, as a main constituent, obtained from the interaction of lipase from *Staphylococcus capitis* with fats and oils have a strong 5α-reductase inhibitory activity. Based on this new finding, the inventors found that the products obtained from the interaction of fats and oils with *Staphylococcus capitis* have an effective action on the growth of hair and also alleviate dandruff and itching (see U.S. patent application Ser. No. 574,132 or European Patent Application No. 84300630.5).

The inventors have further compared the enzyme activities on the scalps of persons with healthy hair and those of persons with unhealthy hair and found that the lipase activity produced by *Staphylococcus capitis* on the scalps of persons with unhealthy hair is lower than those of persons with healthy hair. The inventors then studied properties of the lipase produced by *Staphylococcus capitis* and found that the lipase effectively hydrolyzes lipids excreted from the scalp and contributes to making healthy the scalps and hair roots and that the product of the hydrolysis, i.e., fatty acids, inhibit 5α-reductase.

Lipase (Triacylglycero acylhydrolase El 3.1.1.3) is known to be present widely in living things. The inventors studied the properties of various kinds of lipases from animals, plants, and microorganisms and found these lipases have properties similar to those of lipase produced by *Staphylococcus capitis* relating to action on the scalps and lipids excreted from the scalps. On the basis of this finding, the present invention was completed.

The lipases useful for the hair treatment composition of the present invention are not limited to those from special origins and include lipases from plants, such as rice bran lipase; lipases from animals, such as swine pancreas lipase; and lipases from microorganisms such as lipases produced by *Staphylococcus capitis*, *Rhyzopus delemer*, *Candida cylindracea* etc. However, lipases from plants known so far easily become inactive and are not easily available. Therefore, from a practical standpoint, lipases from animals or lipases from microorganisms are preferably used. Either a single lipase or a combination of two or more lipases can be used.

According to the present invention, the lipase can be used in a highly purified form or in a partially purified form in various grades, so long as it does not contain impurities with undesirable side effects. For example, the following enzyme products can be used: extracts from animal tissues, plants, or cells of microorganisms; or crude enzyme products obtained from such extracts by any conventional methods such as salting-out using inorganic salts, e.g., ammonium sulfate; precipitation with organic solvents, e.g., acetone or ethanol; or purified enzyme products purified by, for example, column chromatography, e.g., column chromatography on diethylaminoethyl (DEAE) cellulose.

The hair treatment compositions according to the present invention can be the above-mentioned lipase or lipase-containing product, but preferably comprises the lipase or lipase-containing product and any conventional base material of a hair treatment composition.

The hair treatment composition should maintain the lipase activity until it is used. Such a hair treatment composition can be a liquid or solid preparation. A liquid preparation is, for example, an aqueous solution containing lipase or an aqueous suspension containing lipase-containing particulate products. The base material of such a liquid preparation is, for example, a buffer solution suitable for maintaining the lipase activity, such as a phosphate buffer having a pH of 5 to 9.

The solid preparation may be a powder, micro-capsule, tablet, granule, or disk. The powder can be produced by mixing purified lipase powder or lipase-containing crude powder produced, for example, by lyophilization, with conventional base materials such as talc, sorbitol, kaolin, or magnesium carbonate. The tablet, granule, and micro-capsule can also be produced from the above-mentioned lipase product or lipase-containing crude product and the above-mentioned base materials according to conventional methods for production of such preparations. The disk can be produced by impregnating an absorbent paper disk with an aqueous solution or suspension containing lipase and drying the impregnated disk by a method which does not inactivate the lipase, such as vacuum drying at low temperature, or lyophilization.

The hair treatment composition of the present invention can also be produced by mixing the purified lipase or crude lipase product with a conventional hair treatment composition such as a hair treatment liquid, hair lotion, shampoo, or hair rinse.

The content of lipase in the present hair treatment composition is not limited, because lipase has substantially no toxicity. However, when the hair treatment composition is a tablet or disk, for convenience in use, the tablet or disk may preferably contain about 0.001 to 50 international units (IU) of lipase.

The unit dose of lipase of the hair treatment composition is preferably 0.001 to 50 IU. That is, the inventors measured the total amount of triglyceride on the scalps of several subjects and found that while there were differences depending on the individual, the amount was about 15 to 30$\mu$ moles. When a hair treatment liquid-type hair treatment composition of the present invention is applied on the scalp and washed away after a short period of time, a single dose of lipase is preferably about 1 to 50 IU. The toxicity test carried out by the inventors and described afterward in detail revealed that application of lipase in 50 IU is nontoxic. When a lotion-type hair treatment composition is applied to the scalp and left for a long period of time, the unit dose of lipase is preferably about 0.001 to 2 IU.

A liquid preparation of the present invention may, if desired, be diluted with water before application. A powder or tablet is dissolved or suspended in water before application. In the case of a disk preparation, lipase impregnated in the disk is eluted with water, and an aqueous solution containing lipase is obtained. The aqueous solution is then applied immediately on the scalp or is mixed with a conventional hair treatment composition such as hair treatment liquid, hair lotion, shampoo, or hair rinse before application to the head.

The hair growth effect of the active ingredients used in the present invention is not clearly understood, but an attempted explanation is given hereinbelow, without prejudice to the present invention.

Various theories have been proposed relating to the causes of depilation, epilation, dandruff, and itching. For example, an unbalanced hormone constitution theory, a nutrient relating theory, a seborrhea theory, and a genetic or hereditary theory are known. It appears that there is a high correlation between the above-mentioned abnormal conditions and the development of glandula sebacea (see Masumi Inaba, "Mainichi Life" November, 1981, pages 26 to 35; "Saishin Keshohin Kagaku (Recent Cosmetics Science)", pages 130 published by Yakuji Nippo Sha in 1980; Kenji Adachi et. al., "Biochemical and Biophysical Research Communication", 41 (4), pages 884 to 890 (1970); Susumu Takayasu et. al., Journal of Investigative Dermatology, 74, pages 187 to 191, 1980).

That is, when the glandula sebacea of a head portion is developed by nutrients, hormones, or the like, testosteron is converted to stronger 5$\alpha$-dihydrotestosteron by 5$\alpha$-reductase present in the glandula sebacea. This is transferred to hair papilla via blood vessels, thereby alleviating the activities of adenylcyclase in hair-matrix cells. As a result, it is believed that the size of hair-follicles is gradually reduced, causing involution and, therefore, the hair becomes thin and downy, eventually leading to baldness.

On the other hand, dandruff is formed because selium is secreted and exudated to the surface of scalp in a large amount, due to the hypertrophy of glandula sebacea, and is mixed with horney or keratin peeled from the surface of the scalp. The dandruff thus formed inhibits dermal of skin respiration and the intake of nutrients into the fibril (or hair-root) portions. This also causes baldness.

Based on these mechanisms for generating depilation, epilation, and dandruff, lipase activity, which decomposes the lipid from the glandula sebacea, and 5$\alpha$-reductase inhibitory activity are important and essential characteristics and properties which the hair treatment compositions should have. These activities also become one standard or criterion for scientifically evaluating the effect of the hair treatment or hair dressing compositions.

As mentioned above, lipase used in the present invention hydrolyzes lipids excreted from and adhered on the scalp to generate fatty acids and eliminate the inhibition on skin-respiration. The hydrolyzation products, i.e., the fatty acids, have a strong 5$\alpha$-reductase inhibiting activity.

Prevention of generation of dandruff and itching on the scalp and the strong hair growth effect of the present hair treatment composition is believed to be caused by the above-mentioned mechanism due to the 5$\alpha$-reductase inhibitory activity. Furthermore, the microflora of the scalp is maintained in or brought to a healthy state by the fatty acids derived from lipides by the hair treatment composition according to the present invention. It is considered that when these actions or functions are combined or multiplied, they exhibit a strong hair growth acceleration effect.

When the hair treatment composition according to the present invention is applied to the human scalp or animal skins, strong hair growth acceleration effects can be provided. That is, when the hair treatment composition according to the present invention is applied to the human scalp, depilation and epilation can be effectively alleviated, downy hairs become healthy, and the generation of dandruff and itching can be prevented.

The nonpathogenicity of the hair treatment composition according to the present invention has been confirmed. That is, cellulose disks 6 mm in diameter and 1 mm in thickness impregnated with 20 $\mu$l of 0.02 M phosphate buffer (pH 8.0) containing 2,500 IU/ml of lipase from *Staphylococcus capitis* obtained according to example 1 or with 20 $\mu$l of 0.05 M phosphate buffer (pH 6.0) containing 5,000 IU/ml of lipase from *Candida cylindracea*, were put on the inside upper arms of 10 humans or the shorn backs of of four rabbits and fixed with tape. The cellulose disks were replaced once a day for three days. Cellulose disks impregnated with the above-mentioned buffers but containing no lipase were used as a control.

No abnormal conditions were found in any case.

The 5α-reductase inhibitory activity was determined as follows.

Prostate gland cells of rats were crushed and a specimen of testosterone 5α-reductase was then prepared by separating microsome from the crushed liquid mixture. The conversion of the testosterone to 5α-dihydrotestosterone by the use of the above-prepared enzyme specimen was monitored by radioisotopically labelled testosterone. The reaction mixture was extracted with ethyl acetate and the extract was developed twice by silica gel thin layer chromatography (solvent system, dichloromethane:cyclohexane:acetone=15:4:1). The amount of 5α-dihydrotestosterone was determined from the intensities of the radioactivity.

Reaction

A 30 μl amount of a 0.05 M phosphate buffer (pH=6.6), 10 μl of an enzyme specimen, 8.5 pmol of labelled testosterone, 50 nmol of a reduced form of NADP (nicotinamide adenine dinucleotide phosphate), and 10 μl of a test sample were mixed (final volume =50 μl). The mixture was incubated at a temperature of 25° C. for 60 minutes.

The reaction was stopped by the addition of 100 μl of ethyl acetate, and the reaction mixture was extracted by vigorous shaking. The extract was developed in the same manner as mentioned above, and the intensity of the radioisotope was measured by using a scintillation counter.

The above-mentioned determination was applied to samples having various concentrations. The 5α-reductase inhibitory activity was obtained as an a 50% inhibitory concentration ($IC_{50}$).

The 5α-reductase inhibitory activity $IC_{50}$ of the fatty acids are, for example, as follows:

| Fatty Acid | $IC_{50}$ (mM) |
|---|---|
| Linoleic acid | 0.18 |
| Oleic acid | 0.32 |
| Linolenic acid | 1.6 |
| Palmitoleic acid | 0.18 |
| n-Capric acid | 0.5 |
| n-Caprylic acid | 1.7 |
| Lauric acid | 0.6 |
| Myristic acid | 1.8 |
| Palmitic acid | 0.3 |
| Stearic acid | 1.3 |

EXAMPLES

The present invention will now be further illustrated by, but is by no means limited to, the following examples, in which the preparation, application, and effect of the hair treatment composition of the present invention are specifically disclosed.

EXAMPLE 1

Preparation of lipase from *Staphyloccus capitis*

To 38 shaking flasks containing culture medium comprising soy bean peptone and sodium chloride, pure culture of *Staphylococcus capitis* ATCC 27840 was inoculated. The culture media were incubated at 30° C. for 24 hours while shaking. The cultured media were then combined and centrifuged.

To the supernatant, ammonium sulfate was dissolved to 75% saturation. The mixture so obtained was stirred with a stirrer at 5° C. overnight, preventing formation of foam and centrifuged at 7000 rpm for 30 minutes to collect a precipitate, which was then dissolved in 20 mM phosphate buffer with pH 7.0. The solution was put into a dialysis tube, dialyzed against 3 l of the same buffer for three hours, against 3 l of the same fresh buffer for three hours, and finally against 10 l of the same fresh buffer overnight. The dialyzed solution in the dialysis tube was removed and the solution was centrifuged at 10,000 rpm for 50 minutes to obtain a supernatant.

The supernatant was applied to DEAE cellulose of the OH type equilibrated with the above-mentioned phosphate buffer and filled in a column of 3.6 ×21 cm. The column was washed with the same buffer, then eluted with 1 l of the same buffer with a gradient concentration of from 0 to 1 M sodium chloride to obtain 80 ml of a fraction with lipase activity.

The fraction was concentrated to 8 ml by ultrafiltration. The concentrated fraction was then applied to an Ultrogel (Trademark of products of L'industrie Biologique Francaise, France) AcA34 column of 2.5×40 cm and eluted with the above-mentioned phosphate buffer to obtain 40 ml of an active fraction. The fraction contained 6300 IU. The fraction was dialysed to desalt and lyophiled to obtain 29.5 mg of crude lipase preparation.

EXAMPLE 2

The crude lipase preparation obtained according to Example 1 was dissolved in water to a concentration of lipase of 1.0 IU, and 20 μl of the solution was impregnated in paper disks of 6 mm in diameter and 1 mm in thickness. The wet paper disks were frozen and lyophilized to obtain dried disks carrying lipase for use as a lotion-type preparation. The preparation can be used by immersing it in water to obtain a solution containing lipase activity, which then is used as a hair lotion.

EXAMPLE 3

To paper disks prepared in Example 2, 3 ml amounts of water were added. The obtained solutions were applied to the scalps of 10 men, each suffering from a large degree of itching, dandruff, and depilation at ages of 24 to 50, once a day for one month.

The results were as follows:

| Condition | Excellent | Effect Good | None |
|---|---|---|---|
| Dandruff | 8 | 2 | 2 |
| Itching | 6 | 3 | 1 |
| Depilation | 5 | 3 | 2 |

EXAMPLE 4

The following ingredients:

| | |
|---|---|
| Magnesium silicate | 35 g |
| Lipase (swine pancreas lipase; Signa Chemicals Company, USA) | 200 I.U. |
| Solution of gum arabic (10 g of gum arabic in 0.2 M phosphate buffer pH 6.5) | | are thoroughly kneaded. The obtained mass was passed through a No. 16 sieve (JIS Z 8801) to form granules, which were dried in air. About 45 g of granulate preparation for hair treatment liquid type was obtained.

EXAMPLE 5

To 0.5 g of granulate preparations as obtained in Example 4, 4 ml amounts of water were added to dissolve the preparations. The obtained solutions were rubbed on the heads of 10 men, each suffering from a large degree of itching, dandruff, and depilation, at ages of 24 to 50, every other day for one month.

The results were as follows:

| Condition | Excellent | Good | None |
|---|---|---|---|
| Dandruff | 6 | 3 | 1 |
| Itching | 7 | 1 | 2 |
| Depilation | 4 | 4 | 2 |

We claim:

1. A hair treatment composition for suppression of dandruff and itching of the scalp comprising lipase, wherein the lipase is one produced by microorganism selected from the group consisting of *Staphylococcus capitis*, *Rhyzopus delemer*, and *Candida cyclindracea* or obtained from swine pancreas, wherein the content of lipase is about 0.001 to about 50 IU in a single dose.

2. A hair treatment composition as claimed in claim 1, wherein the hair treatment composition is in a form selected from the group consisting of solutions, suspensions, powders, micro-capsules, tablets, granules, and disks.

3. A hair treatment composition as claimed in claim 2, wherein the disks are in unit dose forms.

4. A hair treatment composition as claimed in claim 2, wherein the hair treatment composition is in a form selected from the group consisting of powders, solutions, suspensions, granules, and disks.

5. A hair treatment composition as claimed in claim 1 wherein the composition is in a form selected from the group consisting of hair treatmewnt liquid and hair lotion.

6. A method for suppression of dandruff and itching of the scalp comprising applying to the scalp a composition comprising lipase, wherein the lipase is one produced by a microorganism selected from the group consisting of *Staphylococcus capitis*, *Rhyzopus delemer*, and *Candida cylindracea* or obtained from swine pancreas, the amount of lipase being 0.001 to 50 IU in a single dose.

* * * * *